United States Patent [19]
McFarlin et al.

[11] Patent Number: 5,127,393
[45] Date of Patent: Jul. 7, 1992

[54] FLEXIBLE ENDOSCOPE WITH RIGID INTRODUCER

[75] Inventors: Whitney A. McFarlin, Minneapolis; Rick L. Shockey, Coon Rapids, both of Minn.

[73] Assignee: Medilase, Inc., Plymouth, Minn.

[21] Appl. No.: 706,339

[22] Filed: May 28, 1991

[51] Int. Cl.⁵ .............................................. A61B 17/32
[52] U.S. Cl. ........................................ 128/4; 128/7; 604/158
[58] Field of Search ................... 128/4, 7-9; 604/158, 264, 280-284

[56] References Cited

U.S. PATENT DOCUMENTS

| | | |
|---|---|---|
| 4,802,461 | 2/1989 | Cho .......................................... 128/7 |
| 4,911,148 | 3/1990 | Sosnowski et al. ................. 128/7 X |
| 4,986,258 | 1/1991 | Cho et al. ............................ 128/7 |
| 5,024,655 | 6/1991 | Freeman et al. ................ 604/158 X |

*Primary Examiner*—Robert Bahr
*Assistant Examiner*—J. Doyle
*Attorney, Agent, or Firm*—Haugen and Nikolai

[57] ABSTRACT

To facilitate certain surgical procedures, a flexible endoscope may more readily be passed through body vessels and tubular organs, especially when those organs assume a tortuous path. However, a difficulty arises in steering a flexible endoscope through internal body orifices. In accordance with the present invention, a rigid introducer is used in combination with the flexible endoscope to facilitate targeting of such an orifice and once the distal end of the introducer is made to enter the orifice, the flexible endoscope can be advanced through the introducer and there beyond to the point in the body where an item of interest is to be viewed.

11 Claims, 2 Drawing Sheets

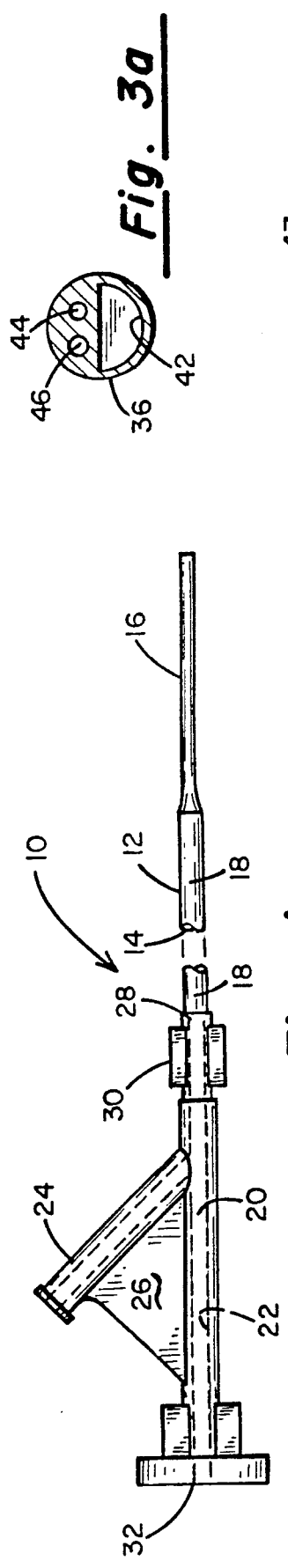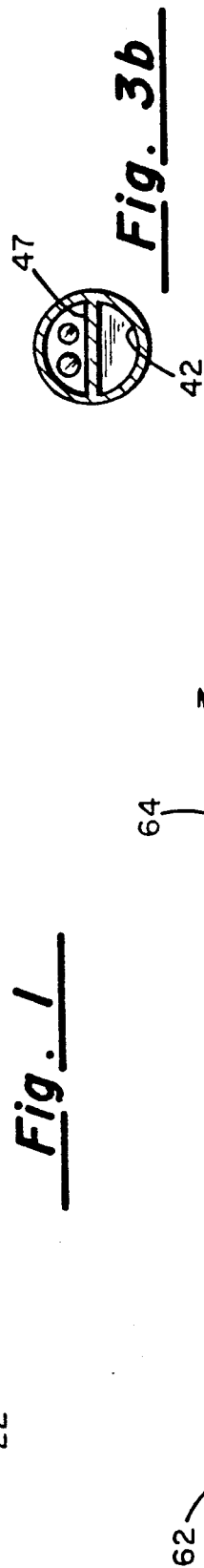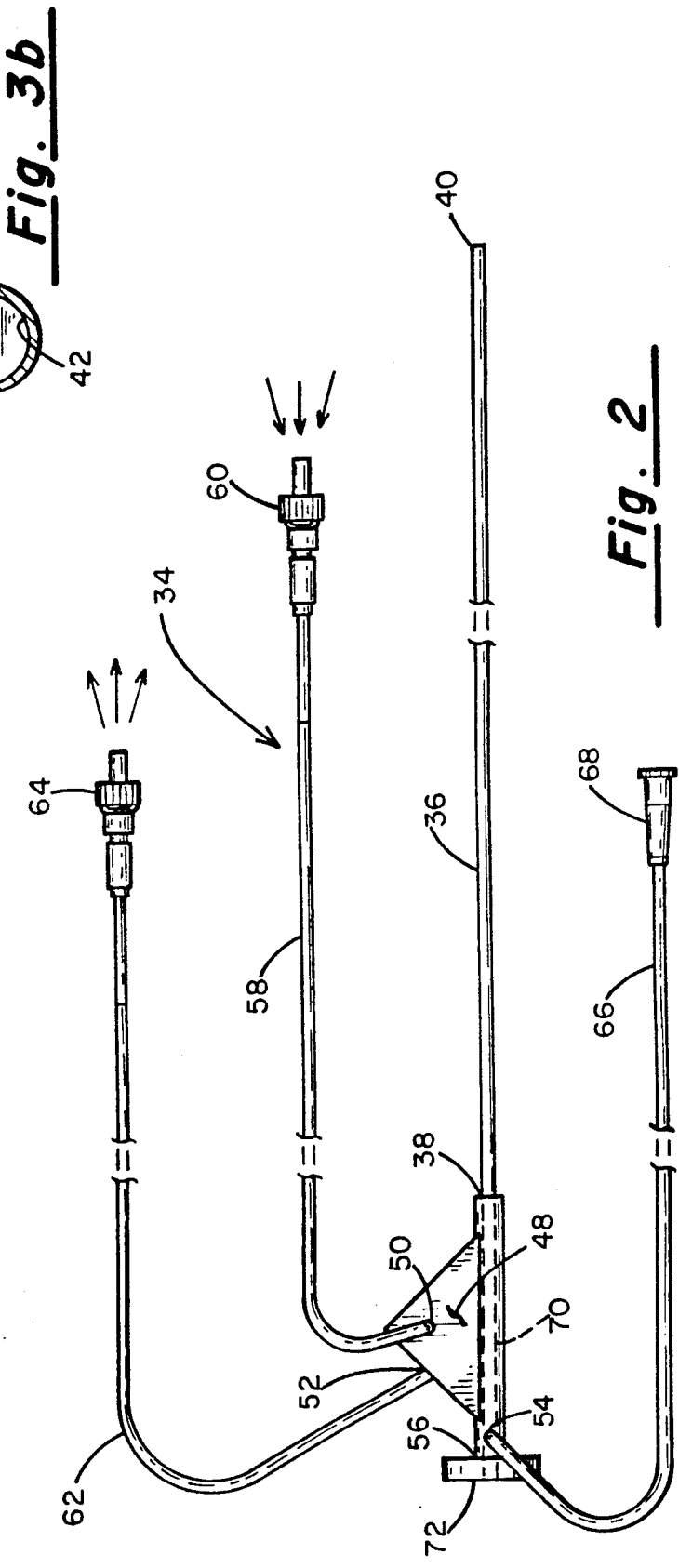

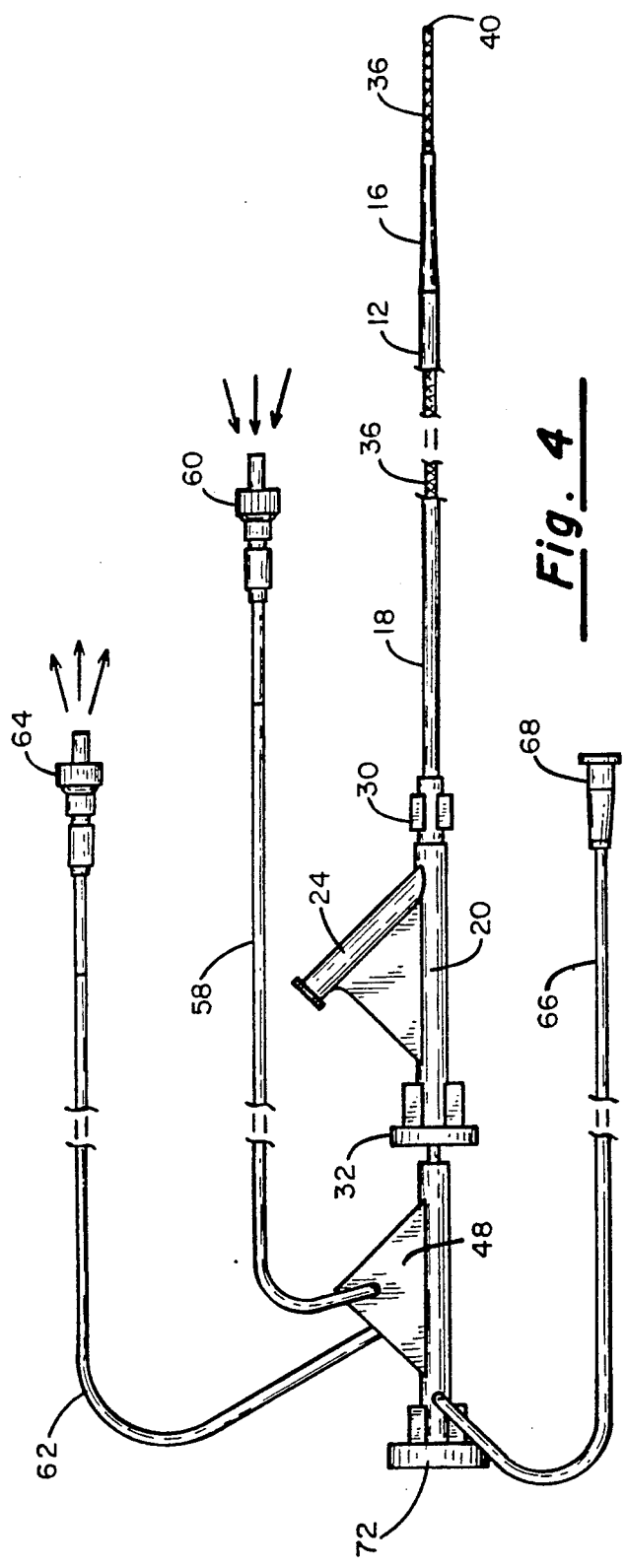
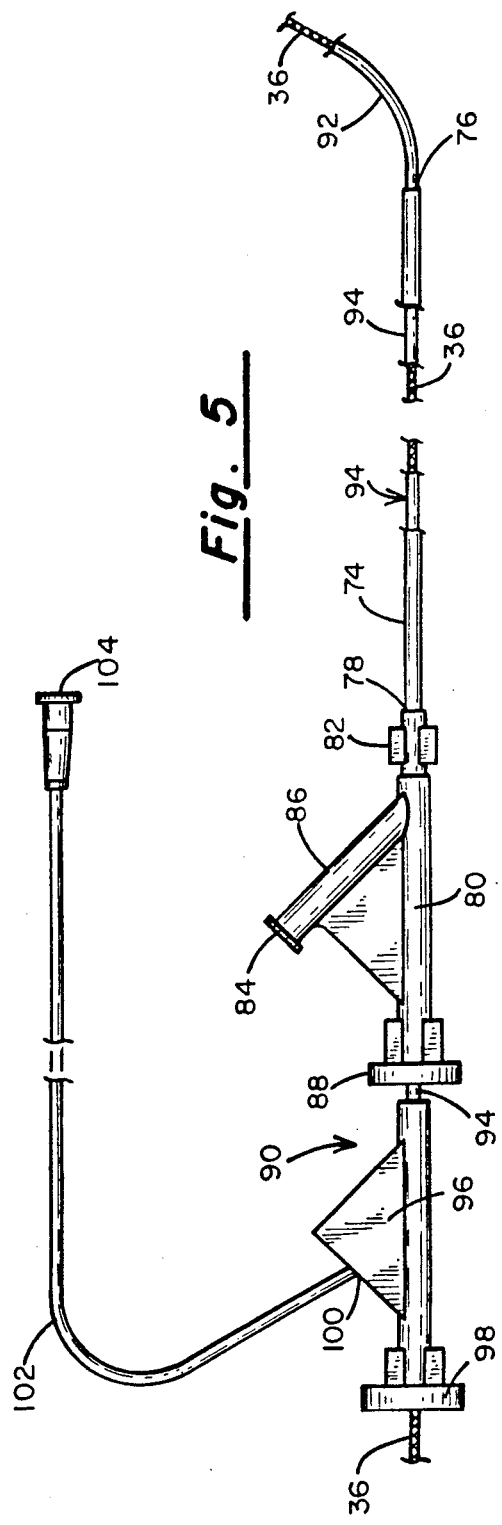
Fig. 4
Fig. 5

FLEXIBLE ENDOSCOPE WITH RIGID INTRODUCER

BACKGROUND OF THE INVENTION

I. Field of the Invention

This invention relates generally to medical apparatus for diagnosing and treating abnormalities in internal body organs, and more particularly to a flexible endoscope used in combination with a rigid introducer for more readily gaining access to the site within the body to be viewed and treated.

II. Discussion of the Prior Art

Many forms of endoscopes are known in the art. They generally comprise an elongated multi-lumen tube having a proximal end and a distal end. Included among the plural lumens is one containing an optical fiber or bundle of such fibers for transmitting light from a light source coupled to the proximal end of the tube to the distal tip for illuminating the vessel or organ cavity to be examined. Another lumen is typically used to contain a further optical fiber for transmitting the illuminated image to an eye piece or other viewing device coupled to the proximal end of the endoscope. An endoscope will further typically include a lumen comprising the working channel through which flushing liquid may be injected and aspirated and that working channel may also provide a pathway through which other instruments may be passed through the body to the location where the treatment is to be effected.

The tube comprising the endoscope may be rigid as in U.S. Pat. No. 4,986,258 to Cho et al. assigned to the Candela Laser Corporation of Wayland, Massachusetts, or, alternatively, may comprise a flexible tube as in the Foerster et al. U.S. Pat. No. 4,905,667. Rigid endoscopes are appropriate only when the passageway through the body is straight or linear while flexible endoscopes can be used in traversing a more tortuous path. There are medical procedures, however, where a rigid endoscope has advantages as regards certain aspects thereof while the flexible properties of a flexible endoscope may also prove advantageous for other phases of that procedure.

For example, when conducting an examination or treatment in the kidneys, an endoscope must be routed through the urethra, across the bladder, into the ostia of one or the other of the two ureters, through the selected ureter into the right or left kidney. Typically, the endoscope may be used to view kidney stones and then an appropriate instrument may be routed through the working channel of the endoscope to fragment or capture a stone to be removed. While a flexible endoscope may be readily passed through the urethra, it proves difficult to thread the flexible tube across the expanse of the bladder and then manipulate the flexible end into the desired ureter ostium. In this phase of the procedure, a rigid endoscope proves more workable because it can span the bladder without sagging. Thus, the device as described in the above-referenced Cho et al. Patent allows a physician to more readily position the distal or viewing end of the endoscope into a ureter. However, because of the curvature of the ureter proximate the pubic arch, it is most difficult to advance a rigid catheter beyond that point and into the kidney. In fact, because of the limitations placed upon the wall thickness of the rigid catheter by the dimensions of the tubular body passages to be traversed (the urethra and ureter) and the sizes of the lumens required in the endoscope for illumination, imaging and working, it has happened that rigid endoscopes have actually fractured when an attempt is made to traverse the curved portion of the ureter with that rigid instrument.

It can be appreciated, then, that neither a rigid nor a flexible endoscope is suitable for all phases of certain endoscopic procedures.

OBJECTS

It is accordingly a principal object of the present invention to provide a combination of instruments which may be utilized in such procedures to achieve the respective benefits of both rigid and flexible endoscopes.

Another object of the invention is to provide the combination of a rigid tubular introducer and a flexible endoscope where the introducer has a central lumen of a size permitting the flexible endoscope to be passed therealong.

Still another object of the invention is to provide the combination of a rigid tubular introducer and a flexible endoscope where the flexible endoscope is of a length exceeding that of the introducer and of an outside diameter permitting it to be readily advanced through and beyond the distal end of the introducer.

SUMMARY OF THE INVENTION

In accordance with the present invention, there is provided an elongated, rigid, tubular introducer whose outside diameter may be stepped or continuously tapered but having an internal lumen of a uniform diameter extending from the proximal end to the distal end of that introducer. A Tuohy-Borst-type hub is preferably affixed to the proximal end of the introducer. The overall length of the introducer will vary depending upon the surgical procedure to be effected.

The flexible endoscope comprises an elongated flexible plastic tube, preferably formed from polyurethane, polyethylene or another suitable plastic and effectively partitioned into two or more lumens. One lumen of a bilumen tube is for accommodating optical fiber(s) or light pipe for transmitting light from the proximal end and a second lumen carries another light pipe or optical fiber(s) for transmitting the image being viewed from the distal end of the endoscope back to an eye piece or other viewing device coupled to the proximal end thereof. The endoscope will also include at least one additional lumen serving as the working channel. In a trilumen version, the light fiber(s) and the image fiber(s) may reside in separate lumens.

The outside dimension of the tube comprising the flexible endoscope is less than the internal diameter of the lumen in the rigid introducer, allowing the flexible endoscope to be fed through the Tuohy-Borst-type clamp and down the central lumen of the rigid introducer. The overall length of the flexible endoscope is greater than the length of the introducer such that if the flexible endoscope is fed down through the introducer, its flexible distal of the introducer.

When carrying out a urological procedure, then, the rigid introducer may first be inserted through the urethra and across the expanse of the bladder. By appropriately manipulating the proximal end, its distal end is inserted through an ostium and a short distal portion thereof is made to enter the desired one of the ureters. Now, the flexible endoscope may readily be advanced beyond the distal end of the introducer until the flexible distal portion thereof traverses the curved portion of the ureter and is made to enter the kidney. Once so positioned, the Tuohy-Borst-type clamp on the introducer can be tightened so as to grip the flexible endoscope and inhibit unintentional displacement of the flexible endoscope during subsequent procedures.

It is also a feature of the present invention that the flexible tubular portion of the endoscope be separable from the proximal hub structure containing the optics. In this fashion, the endoscope may be fabricated at such a low cost that it can be disposed of after a single use while the more expensive optical structures are retained.

DESCRIPTION OF THE DRAWINGS

Further details, objects and advantages of the invention will become apparent to those skilled in the art from the following detailed description of a preferred embodiment in which like numerals in the several views refer to corresponding parts.

FIG. 1 is a side elevation of the insertion guide sheath or introducer;

FIG. 2 is a side elevation of the flexible endoscopy catheter;

FIG. 3a is a distal end view of the flexible endoscope of FIG. 2 where a trilumen tube is employed;

FIG. 3b is a distal end view of the flexible endoscope of FIG. 2 when a bilumen tube is employed;

FIG. 4 is a view showing the assembly of the introducer of FIG. 1 with the catheter of FIG. 2 installed therein; and FIG. 5 shows an alternative embodiment of the invention having a sheath or introducer with a curved tip and containing the endoscopic catheter of FIG. 2.

DESCRIPTION OF THE PREFERRED EMBODIMENT

Referring first to FIG. 1, there is a shown a partially sectioned, side elevation view of the insertion guide sheath used with the flexible endoscope in accordance with the present invention. The insertion guide sheath is indicated generally by numeral 10 and comprises an elongated, single-lumen tube 12 which is preferably formed from stainless steel or a suitable medical grade plastic such as a polycarbonate or a polyester and the plastic may be reinforced with a suitable fiber material if necessary to provide strength While the lumen 14 may be of uniform size throughout the length of the tube 12, the outer dimension thereof may be stepped or tapered such that the distal portion 16 is of a lesser outside diameter than the more proximal segment or portion 18. While the outside diameters of the portion 16 and 18 as well as the internal diameter of the lumen 14 may vary depending upon the end use of the instrument, the wall thickness of the segment 18 may be in the range of from 0.050 inch down to 0.030 inch, while the wall thickness in the segment 16 may vary between 0.019inch and 0.005 inch. In terms of overall length, the segment 18 may be about 9.5 inches and that of segment 16, approximately 3.0 inches where the instrument is to be used in urology.

Affixed to the proximal end of the tubular member 12 is a molded plastic hub indicated generally by numeral 20. Extending the full length of the hub 20 is a longitudinal bore 22 through which a flexible endoscope may be introduced, all as described in considerably greater detail hereinbelow. The bore 22 is in general alignment with the lumen 14 of the rigid tubular member 12. Extending at a predetermined angle to the length dimension of the hub 20 and integrally formed with the hub is a tubular stem 24. The lumen of the stem 24 intersects with the longitudinal bore 22 and allows a flushing liquid to be injected into that bore and down the lumen 14 of the tubular segment 12. A triangular gusset 26 is integrally molded between the stem 24 and the remainder of the hub 20 to provide mechanical support and rigidity to the stem 24.

Surrounding the distal portion 28 of the stem 20 is a rotatable swivel 30. When the swivel 30 is gripped between the surgeon's thumb and forefinger, the hub member 20 can be rotated which, as will be more fully explained, allows limited steering of the flexible endoscope when it is passed through the introducer of FIG. 1 with a distal end portion thereof extending beyond the digital end of the introducer 10.

Also rotatably affixed to the proximal end of the molded plastic hub 20 is a Tuohy-Borst type clamp 32 which, when released, allows longitudinal translation of an endoscope or other instrument relative to the introducer sheath 10. However, when the Tuohy-Borst type clamp 32 is engaged, it firmly clamps the endoscope or other instrument inserted through the hub 20 and down the rigid tubular member 12.

Referring next to FIG. 2, there is illustrated a side elevation view of the flexible endoscopy catheter constructed in accordance with the present invention for use with the rigid tubular introducer of FIG. 11. The flexible endoscopy catheter is indicated generally by numeral 34 and comprises an elongated flexible multilumen tube 36 having a proximal end 38 and a distal end 40. The tube is preferably an extruded thermoplastic, such as polyurethane or polyvinylchloride.

As shown in FIG. 3a, the tubular member 36 includes a working channel or lumen 42, an illumination channel or lumen 44 and an image channel or lumen 46. The working channel 42 is shown as being generally semicircular in shape and is opened from its proximal end to its distal end for accommodating the passage of working tools (not shown) therethrough. The illumination channel 44 includes an optical fiber or bundle of such fibers for transmitting light from the proximal end 38 of the tube to and beyond the distal end 40. The image channel 46 also includes a fiber-optic medium having a lens on its distal end which is used to transmit an image illuminated by the light emanating from the bundle 44 back through the tubular member 36 to the proximal end thereof. FIG. 3b illustrates that the tube 36 may be a bilumen configuration with the light fiber and image fiber occupying the same lumen 47. Those skilled in the art will appreciate that the tube 36 may have a single lumen containing the optical fibers for both the illumination and the image and an additional coaxially disposed tube as the working channel or as an irrigation-/aspiration vehicle.

The outside diameter of the flexible endoscope tube 36 may range in size from 0.118 inch (9 Fr.) to a diameter of 0.039 inch (3 Fr.). The working lumens may then be approximately 0.086 inch (6.6 Fr.) to 0.020 inch (1½ Fr.), respectively. The tubular member 36 may typically be in the range of from 20 inches 35 inches long.

Affixed to the proximal end 38 of the tubular member 36 is a molded plastic hub 48 having two optical ports 50 and 52, a fluid port 54 and an instrument port 56. A short length of optical fiber contained within an opaque sheath 58 allows the hub 48 to be joined to a light source via a coupler 60. Within the hub 48, the optical fiber 58 optically joins with the optical fiber or bundle within the lumen 44 of the flexible tube 36. In a similar fashion, the image optical fiber or bundle in the lumen 46 of the tube 36 is optically coupled to a similar fiber-optic light conductor 62 terminating in a connector 64 for facilitating the coupling of the endoscope to a lens system or other form of optical display whereby the image viewed by the distal end 40 of the endoscope can be observed.

A plastic tube 66 having a luer fitting 68 attached to the free end thereof couples to the fluid port 54 on the hub 48. This tube is in fluid communication with the working lumen 42 of the flexible endoscope tube 36 allowing a syringe filled with saline to be used to force the saline through the working channel of the endoscope to flush the site being observed. The luer fitting 68 may also be coupled to a suction source whereby body fluids and any flush liquid can be aspirated from the site in the body being observed.

Extending longitudinally through the hub 48 is a bore 70 which is generally aligned with the working channel 42 in the flexible tubular endoscope 36. As such, working instruments, such as a laser fiber, an electrosurgical instrument, or other surgical device may be passed through a Tuohy-Borst type clamp 72 and through the bore 70 and the working lumen 42. By rotating the clamp member 72, the instrument employed can be locked in place against longitudinal displacement.

With reference to FIG. 4, in carrying out a surgical procedure such as removal of kidney stones, the flexible endoscope device of FIG. 2 is inserted through the bore 22 in the molded plastic hub 20 to the point where the distal end 40 of the endoscope tube 36 is generally flush with the distal end of the rigid tubular sheath 12. When so inserted, the Tuohy-Borst clamp 32 is tightened down relative to the exterior of the flexible endoscope 36 preventing inadvertent displacement thereof within the introducer sheath. The rigid tubular sheath 12 containing the flexible endoscope tube 36 may then be passed through the urethra and across the bladder with the distal end of the segment 16 being steered so as to enter the ostia of the ureter leading to the kidney where the stone is to be removed. In locating the ostia, the physician may observe the image of the bladder wall which is illuminated by light from the source (not shown) leading to the connector 60. Once the small diameter segment 16 of the rigid tubular introducer 10 is inserted through the ostia and partially into the ureter but short of the pubic arch, the Tuohy-Borst clamp 32 can be released and the endoscope 34 can be advanced in the distal direction such that the flexible tubular body 36 may readily navigate the arch in the ureter to enter the kidney. All the while the endoscope is being positioned, the surgeon is able to view the image picked up by the fiber-optic media in the lumen 46, either through an eye piece or by way of a video camera and display terminal which is joined to the connector 64.

When the distal end 40 of the endoscope is positioned adjacent the stone to be removed, the surgeon may now insert a laser fiber through the Tuohy-Borst clamp 72 on the hub 48 and it will be passed through the working channel 42 (FIG. 3) and appropriately positioned such that when the laser energy is applied, the stone can be fragmented to a size permitting the pieces to be drawn back through the working lumen 42 of the endoscope with the aid of a suction source connected to the luer fitting 68 or by removing the laser fiber from the working channel of the endoscope and replacing it with a suitable instrument for grasping a stone fragment and then retracting that instrument back through the working channel and out the end of the hub 48.

While the use of the rigid introducer and the flexible endoscope has been described in connection with the performance of a urinary procedure, those skilled in the art will appreciate that the invention may find wider application where a rigid introducer allows better control over the positioning of the distal end of an endoscope. For example, the present invention may also be readily used in performing laparoscopic cholecystectomy procedures.

The entire assembly shown in FIG. 4 of the drawings can be fabricated at sufficiently low cost so that it can be treated as a disposable, i.e., a single-use instrument. Because the light source joined to the coupler 60 and the viewing device coupled to the connector 64 for displaying the image can readily be uncoupled from the instrument, the higher cost instrumentation can be reused with a new assembly such as is shown in FIG. 4. This, of course, obviates the need for any resterilization following its use.

ALTERNATIVE EMBODIMENT

Referring to FIG. 5, an arrangement is illustrated which allows a flexible endoscope to be more readily routed to a desired surgical site. For example, when performing a laparoscopic cholecystectomy, an incision must be made in the cystic duct. The common bile duct and the cystic duct must both be inspected for stones prior to completion of the procedure. By utilizing a curved sheath or introducer and a trocar, it becomes possible to pass the curved tip of the introducer and seat it into the cystic duct through the incision. Once the curved introducing sheath is seated in the cystic duct, a flexible endoscope, such as that shown in FIG. 2, may be passed through the curved sheath and advanced into the cystic duct and up to the common bile duct. Then, any stones that may be found may be disintegrated by passing a laser fiber through the working channel of the endoscope and energizing the laser to deliver sufficient energy to the stone to cause it to break up. The stone may also be removed using other techniques or devices passed through the endoscope of the present invention.

Referring to FIG. 5, there is shown an assembly including a generally rigid trocar 74 having a sharpened distal end 76 to facilitate its penetrating the abdominal wall of a patient. The trocar 74 has an internal lumen extending the length thereof and affixed to its proximal end 78 is a molded plastic hub member 80 which may be generally identical to the hub member used with the rigid introducer sheath 10 of FIG. 1. As such, it includes a swivel 82, a luer fitting 84 which is connected to a stem 86 containing a hollow bore which is in fluid communication with the lumen of the trocar 74. Affixed to the proximal end of the hub 80 is a Tuohy-Borst type clamp 88. Extending through the hollow bore of the hub 80 and through the lumen of the trocar 74 is a generally rigid introducer sheath 90 similar to what is shown in the embodiment of FIG. 1 but which includes a pre-formed arcuate distal tip portion 92 integrally formed with a straight tubular segment 94. The tubular sheath introducer 90 is preferably formed from a suitable metal, such as stainless steel, and is of sufficient flexibility proximate its distal end portion 92 to be able to pass through the trocar 74, but because of its memory property, when unconfined by the trocar 74, it assumes the deflected arcuate shape illustrated.

Affixed to the proximal end of the tube 94 is a molded plastic hub 96 having an internal longitudinal bore aligned with the lumen of the tube 94 and a Tuohy-Borst clamping member 98 surrounding that opening. A flush port 100 has a segment of tubing 102 connected thereto, the tube 102 leading to a luer connector 104 through which a flushing liquid can be introduced or aspiration accomplished when a suction source is coupled to it.

The lumen of the tubular segment 94 and the integrally formed arcuate portion 92 is dimensioned to accommodate the passage of the flexible endoscope tube 36 therethrough.

Because of the ability of the distal end portion 92 of the introducer sheath 90 to deflect when extended beyond the distal end 76 of the trocar 74, the curved end portion 92 of the sheath can more easily be made to seat into the cystic duct through an incision made therein. Once the deflecting sheath is so seated, the flexible endoscope tube 36 may be passed through the deflecting sheath with its bent distal tip portion, through the cystic duct, to the common bile duct and down to the sphincter. Any stones that may be located using the endoscope may be broken up by passing a lasing fiber (not shown) through the working channel of the endoscope, all as previously described.

Those skilled in the art can appreciate that the sheath 90 with its deflecting end portion and the endoscope may be assembled outside the body as a set. The distal tip of the endoscope would be placed flush with the distal tip of the curved sheath. The procedure then would continue with advancing this assembly, as a set, through the trocar 74 to the cystic duct incision. This allows viewing in the abdomen while trying to find the incision made in the cystic duct so that the sheath may be seated therein.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An endoscope assembly comprising, in combination:
   (a) a substantially rigid tubular introducer of a predetermined length and having a proximal end, a distal end and a lumen extending therebetween, said introducer having an outside diameter of a size allowing it to pass through a tubular body vessel, said introducer including a hub member having a longitudinal bore aligned with said lumen;
   (b) an endoscope comprising an elongated flexible plastic tubular member of a length greater than said predetermined length of said introducer, an outer dimension less than the cross-sectional dimension of said lumen in said tubular introducer such that at least a portion of said endoscope can be made to slide longitudinally through said introducer, said flexible tubular member having a proximal end, a distal end and at least one lumen extending at least a portion of the length of said flexible tubular member, said tubular member containing a first optical channel for transmitting light from a source near said proximal end thereof to said distal end, and a second optical channel for transmitting an image from said distal end toward said proximal end of said flexible tubular member and a working channel, said endoscope further including a hub member affixed to said proximal end of said flexible plastic tubular member with said hub member including
   (i) a longitudinal bore aligned with said working channel,
   (ii) means for optically coupling said source to said first optical channel, and
   (iii) means for optically coupling viewing means to said second optical channel.

2. The endoscope assembly as in claim 1 and further including a port on said hub member on said proximal end of said rigid introducer.

3. The endoscope assembly as in claim 1 and further including a tubular sleeve rotatably affixed to said rigid introducer adjacent to and distal of said hub member on said introducer.

4. The endoscope assembly as in claim 1 wherein said rigid tubular introducer comprises plural segments of decreasing outside dimension, with the distalmost segment being of a lesser dimension than a more proximal segment.

5. The endoscope assembly as in claim 1 and further including a flush/aspirate port formed in said hub affixed to said proximal end of said flexible tubular member and in fluid communication with said working channel.

6. The endoscope assembly as in claim 1 further comprising clamping means in said bore of said hub member on said introducer which engages said flexible tubular member when said endoscope is inserted into said lumen of said rigid introducer to inhibit longitudinal displacement of said flexible tubular member relative to said rigid introducer.

7. The endoscope assembly as in claim 1 wherein said flexible plastic tubular member includes plural lumens and said first and second optical channels reside in separate ones of said plural lumens.

8. The endoscope assembly as in claim 1 wherein said substantially rigid introducer has a curved distal end portion when unconstrained.

9. The endoscope assembly as in claim 1 wherein said hub on said flexible tubular member includes clamping means operatively disposed within said longitudinal bore.

10. The endoscope assembly as in claim 1 wherein said flexible plastic tubular member includes a plurality of lumens for accommodating said first and second optical channels and said working channel.

11. The endoscope assembly as in claim 1 and further including a manually actuatable clamping means operatively disposed in said bore of said hub member of said introducer.

* * * * *